Nov. 1, 1960 D. H. MOREY, JR Plant Pat. 1,982
ROSE PLANT
Filed Jan. 28, 1960
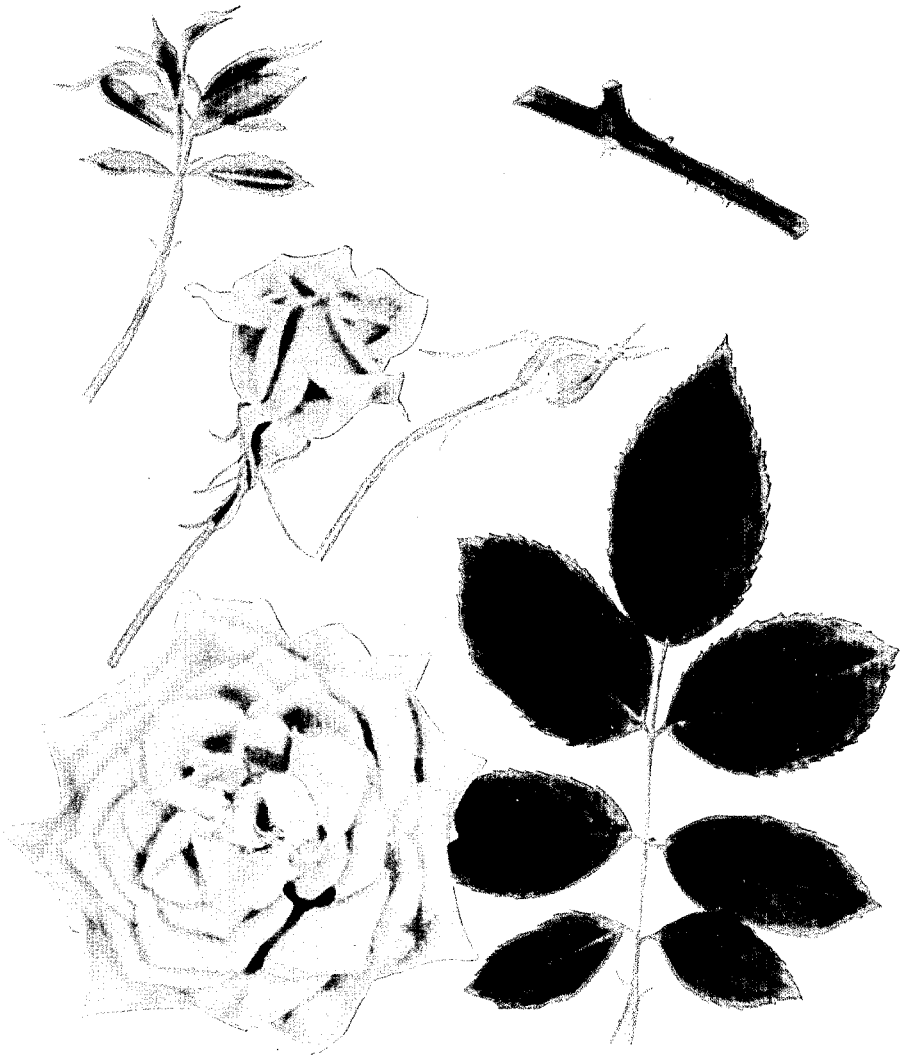
INVENTOR
D. H. Morey, Jr.
BY Robb & Robb
ATTORNEYS United States Patent Office Plant Pat. 1,982
Patented Nov. 1, 1960

1,982

ROSE PLANT

Dennison H. Morey, Jr., Pleasanton, Calif., assignor to Jackson & Perkins Company, Newark, N.Y., a corporation of New York Filed Jan. 28, 1960, Ser. No. 5,325

1 Claim. (Cl. 47—61)

The present invention relates to a new and distinct variety of rose plant of the hybrid tea class, which was originated by me by crossing the variety "Happiness" (Plant Patent No. 911) with the variety "San Fernando" (Plant Patent No. 785).

The primary objective of this breeding was to produce a new variety of rose plant which bears red flowers and is suitable for use as a forcing rose, as well as endowed with greater flower production than the parent variety "Happiness." This objective was fully achieved, along with other desirable improvements, as evidenced by the following unique combination of characteristics which are outstanding in the new variety and which distinguish it from its parents, as well as from all other varieties of which I am aware:

(1) Very prolific cut flower production, which normally averages at least five flowers per plant better than the average production of the well known and popular variety "Better Times" (Plant Patent No. 23);

(2) An attractive and distinctive bud form which is particularly effective as a cut flower;

(3) A distinctive Scarlet-Red, lightly overcast with Rose Red, general tonality of the flowers; and (4) A very strong flower fragrance.

Asexual reproduction of the new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Happiness."
*Pollen parent.*—"San Fernando."
Classification:
*Botanic.*—Hybrid tea.
*Commercial.*—Hybrid tea.

*Flower*

(Observations made from specimens grown in a greenhouse at Newark, New York, in the early afternoon during the latter part of the month of July.)

Blooming habit: Recurrent—continuous.
Bud:
*Size.*—Large.
*Form.*—Ovoid; is not affected by wet or hot weather.
*Color.*—When sepals first divide—Carmine, Plate 1. When petals begin to unfurl—Spectrum Red, Plate 1. When half-blown: inside of petals—Spectrum Red, Plate 1, lightly overcast with Scralet-Red, Plate 1; reverse of petals—Scarlet-Red, Plate 1.
*Sepals.*—Slightly branched; curl back when petals begin to unfurl. Color: inside—Malachite Green, Plate 32; outside—Chromium Green, Plate 32.
*Calyx.* — Color — Chromium Green, Plate 32. Shape — apple. Size — small. Aspect — smooth. Odor when rubbed—none.
*Peduncle.* — Length — medium. Aspect — rough. Strength — erect; slender. Color — Light Bice Green, Plate 31.
*Opening.*—Opens up well; is not affected by adverse weather conditions.

Bloom:
*Size.*—Large. Average size when fully expanded—4½ inches.
*Borne.*—Singly.
*Stems.*—Medium strength; strong.
*Form (when first open).*—High-centered. Permanence—retains its form to the end, but outer petals curl back.
*Petalage.*—Double (full but open center). Number of petals under normal conditions—from 30 to 35.
*Color.*—Center of flower—Spectrum Red, Plate 1, lightly overcast with Rose Red, Plate 12. Outer petals—Carmine, Plate 1, lightly overcast with Spectrum Red, Plate 1. Base of petals (aiglet)—Reed Yellow, Plate 30. Inside of petals—Scarlet-Red, Plate 1, lightly overcast with Rose Red, Plate 12. Reverse of petals—Rose Red, Plate 12. General tonality from a distance—Scarlet-Red, Plate 1, lightly overcast with Rose Red, Plate 12.
*Discoloration.*—General tonality at end of first day—Spectrum Red, Plate 1, lightly overcast with Rose Red, Plate 12. Second day—Spectrum Red, Plate 1, lightly overcast with Rose Red, Plate 12. Third day—Scarlet-Red, Plate 1, lightly overcast with Rose Red, Plate 12.
Petals:
*Texture.*—Leathery; is not affected by wet or hot weather.
*Appearance.*—Inside—velvety. Outside—satiny.
*Form.*—Round; slightly notched.
*Arrangement.*—Imbricated (regularly arranged shingle-like).
*Petaloids in center.*—Few; large.
*Persistence.*—Drop off cleanly.
*Fragrance.*—Strong. Nature—"Old Rose perfume" (centifolia).
*Lasting quality.*—On the plant—very long. As cut flower—very long.

*Genital organs*

Stamens, anthers: Large; many; regularly arranged around styles. Color—Apricot Orange, Plate 14.
Stamens, filaments (threads): Medium length. Color—Spinel Red, Plate 26.
Pollen: Color—Salmon-Buff, Plate 14.
Styles: Bunched; uneven length; short; thin.
Stigmas: Color—Light Ochraceous Buff, Plate 15.
Ovaries: All enclosed in calyx.
Hips: None.
Seeds: None.

*Plant*

Form: Bush.
Growth: Vigorous; upright; bushy.
Foliage: Compound of 3 to 7 leaflets.
*Size.*—Large.
*Quantity.*—Abundant.
*Color.*—New foliage: upper side—Carmine, Plate 1; under side—Brazil Red, Plate 1. Old foliage:

upper side—Dark Green,, Plate 18; under side—Light Bice Green, Plate 17.

*Shape.*—Oval pointed.

*Texture.* — Upper side — leathery. Under side — smooth.

*Ribs and veins.*—Ordinary.

*Edge.*—Serrated (saw toothed).

*Serration.*—Single; small.

*Leaf stem.*—Color—Light Elm Green, Plate 17. Under side—smooth.

*Stipules.*—Medium length; smooth.

Wood:

*New wood.*—Color—Courge Green, Plate 17. Bark—smooth.

*Old wood.* — Color — Varley's Green, Plate 18. Bark—smooth.

Thorns:

*Thorns.*—Quantity: on main stalks from base—ordinary; on laterals from stalk—ordinary. Form— narrow base; short; hooked downward. Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a very prolific cut flower production, an attractive and distinctive bud form which is particularly effective as a cut flower, a distinctive Scarlet-Red, lightly overcast with Rose Red general color tonality of the flowers, and a very strong flower fragrance.

No references cited.